United States Patent
Wang et al.

(10) Patent No.: US 12,379,377 B2
(45) Date of Patent: Aug. 5, 2025

(54) TWO-LAYER MICROFLUIDIC CHIP WITH MAGNETIC BEAD LUMINESCENCE AND DETECTION SYSTEM

(71) Applicant: SHENZHEN WATMIND MEDICAL CO., LTD., Guangdong (CN)

(72) Inventors: Dong Wang, Guangdong (CN); Yuxia Fan, Guangdong (CN); Quan Li, Guangdong (CN)

(73) Assignee: SHENZHEN WATMIND MEDICAL CO., LTD., Shenzhen (CN)

( * ) Notice: Subject to any disclaimer, the term of this patent is extended or adjusted under 35 U.S.C. 154(b) by 876 days.

(21) Appl. No.: 17/623,875

(22) PCT Filed: Oct. 10, 2020

(86) PCT No.: PCT/CN2020/120091
§ 371 (c)(1),
(2) Date: Dec. 29, 2021

(87) PCT Pub. No.: WO2021/068914
PCT Pub. Date: Apr. 15, 2021

(65) Prior Publication Data
US 2022/0357320 A1  Nov. 10, 2022

(30) Foreign Application Priority Data
Oct. 11, 2019 (CN) .......... 201910962678.0

(51) Int. Cl.
*G01N 33/543* (2006.01)
*G01N 33/533* (2006.01)

(52) U.S. Cl.
CPC . *G01N 33/54386* (2013.01); *G01N 33/54326* (2013.01)

(58) Field of Classification Search
None
See application file for complete search history.

(56) References Cited

U.S. PATENT DOCUMENTS

| | | | |
|---|---|---|---|
| 6,454,924 B2 * | 9/2002 | Jedrzejewski | B01L 3/5088 422/50 |
| 8,431,090 B2 * | 4/2013 | Cheung | G01N 33/56977 422/503 |
| 2010/0303687 A1 * | 12/2010 | Blaga | F16K 99/0015 156/247 |
| 2012/0128549 A1 * | 5/2012 | Zhou | F16K 99/0015 422/504 |

\* cited by examiner

*Primary Examiner* — Elizabeth A Robinson
*Assistant Examiner* — Brittany I Fisher

(57) ABSTRACT

Disclosed are a two-layer microfluidic chip with magnetic bead luminescence and a detection system. The chip comprises a top plate and a bottom plate. The top plate comprises a sample addition section, a conjugated ligand storage section, and a sample mixing area, wherein the sample mixing area is in communication respectively with the sample addition section and the conjugated ligand storage section. The bottom plate comprises a flow guiding area, a magnetic bead coating section, a washing area, a detection area, and a washing fluid storage section, wherein the flow guiding area is arranged with a recess that is lower than the bottom wall of the magnetic bead coating section in the height direction, and a flow guiding portion fitted to the recess and connecting the magnetic bead coating section.

15 Claims, 4 Drawing Sheets

TWO-LAYER MICROFLUIDIC CHIP WITH MAGNETIC BEAD LUMINESCENCE AND DETECTION SYSTEM

TECHNICAL FIELD

The present invention relates to the technical field of microfluidic chip-based luminescence immunoassays, and particularly to a two-layer microfluidic chip with magnetic bead luminescence and a detection system.

BACKGROUND

At present, there are two main development trends in In-Vitro Diagnostics (IVD). One is automation and integration, that is, fully automated, highly sensitive large-scale equipment in a central laboratory supporting a large hospital is used to achieve high-precision disease analysis and diagnosis. The other one is miniaturized, bedside analyzers, that is, a small handheld simple device is used to achieve rapid on-site analysis and diagnosis. Due to insufficient funds and low number of samples, small hospitals properly do not purchase expensive large-scale equipment. At present, the rapid detection devices used in most hospitals are mainly test strips and devices matched therewith. However, test strips can only achieve qualitative or semi-quantitative detection, with low detection sensitivity, poor specificity, poor repeatability, and obvious interference. Due to the large population, rise in aging population, and sharp increase in morbidity in China, the dependence on large hospitals is overwhelming. Therefore, it is extremely urgent to develop a fast detection method and device with simple operation, high sensitivity, good repeatability and accurate quantification.

Microfluidic chip technology refers to integration of basic operation units such as sample preparation, reaction, separation, and detection involved in the biological, chemical, and medical analysis processes on a chip on a micrometer scale for performing the entire process of analysis automatically. Due to the huge potential for use in the fields of biology, chemistry, medical science, and others, microfluidic chips have been developed into a multidisciplinary research area of biology, chemistry, medical science, fluid mechanics, material science, and mechanical engineering, and have found use in biomedical research, biochemical test, forensic identification and others. However, the existing microfluidic chip is provided with a top plate and a bottom plate. When a sample flows from the top plate to the bottom plate, because the channels in the bottom plate are at the same level, the sample will automatically flow following the channel due to gravity. For some test items, only a small amount of sample is needed to complete the detection and analysis. If the sample flows from the top plate to the bottom plate and flows directly in the bottom plate, the final test result will be greatly affected, leading to an incorrect test result. In addition, the sample flows along the channel of the bottom plate, the flow path of the sample cannot be confined, so the sample flowing to the detection area cannot be completely filtered, which further affects the final detection result.

SUMMARY

An embodiment of the present invention provides a two-layer microfluidic chip with magnetic bead luminescence and a detection system, to solve the problems that the sample in an existing microfluidic chip flows directly in the bottom plate after flowing from the top plate to the bottom plate, and the flow path of the sample cannot be confined.

The embodiment of the present invention is implemented as follows. A two-layer microfluidic chip with magnetic bead luminescence is provided, which comprises a top plate, comprising a sample addition section, a conjugated ligand storage section, and a sample mixing area, where a conjugated ligand is stored in the conjugated ligand storage section, and the sample mixing area is in communication respectively with the sample addition section and the conjugated ligand storage section; a bottom plate provided on the top plate, comprising a flow guiding area in communication with the sample mixing area, a magnetic bead coating section in communication with the flow guiding area, a washing area in communication with the magnetic bead coating section, a detection area in communication with the washing area, and a washing fluid storage section in communication with the washing area, where the flow guiding area is arranged with a recess that is lower than the bottom wall of the magnetic bead coating section in the height direction, a flow guiding portion fitted to the recess and connecting the magnetic bead coating section, a cut-off groove below a front end of the flow guiding portion, and a barrier portion provided on the flow guiding portion; and a magnetic bead-conjugated ligand is stored in the magnetic bead coating section, and a washing fluid is stored in the washing fluid storage section.

Further more, the top plate further has an air pump communicating with the sample addition section thereon.

Further more, the top plate has an elastic member provided at a corresponding position of the air pump and the sample mixing area.

Further more, a porous elastic member is provided inside the air pump.

Further more, the sample addition section includes a sample addition port and a lid for opening or closing the sample addition port, and the sample addition section further includes a rubber ring provided on the sample addition port.

Further more, both the top plate and the bottom plate are provided with a limiting notch at a position corresponding to each other.

Further more, the top plate is provided with a first buckle or a first slot, and the bottom plate is provided with a second slot or a second buckle. The first buckle mates with the second slot, or the first slot mates with the second buckle, so that the top plate and the bottom plate are fastened.

Further more, a single-sided adhesive material is provided on a part of or the entire surface on at least one side of the bottom plate.

Further more, a product label is provided on the surface of the top plate or the bottom plate, and a two-dimensional code label is provided on the surface of the top plate or the bottom plate.

Further more, the top plate is provided with a magnetic attraction clearance hole on a corresponding track in communication with the magnetic bead coating section, the washing area and the detection area.

Further more, the bottom plate also includes a waste container communicating with the washing area.

Further more, the bottom plate also includes a luminescence liquid storage section communicating with the detection area, and a luminescence liquid is stored in the luminescence liquid storage section.

Further more, the top plate is provided with a washing fluid clearance hole and a luminescence liquid clearance hole at a position corresponding to the washing fluid storage section and the luminescence liquid storage section.

Further more, a fluorescence liquid is stored in the conjugated ligand storage section.

The present invention also provides a two-layer microfluidic detection system with magnetic bead luminescence. The detection system comprises a two-layer microfluidic chip with magnetic bead luminescence as described above; a magnet unit for driving the magnetic beads in the magnetic bead-conjugated ligand solution to move; a squeezing unit for crushing the conjugated ligand storage section and the washing fluid storage section so that the conjugated ligand and the washing fluid flow out; and a detection unit for detecting a light signal emitted from the detection area.

The present invention has the following beneficial effects. Compared with the prior art, a two-layer microfluidic chip with magnetic bead luminescence and a detection system are designed. A sample enters the chip from a sample addition section, is mixed with a conjugated ligand in a sample mixing area, and then enters a recess in a flow guiding area. Because the recess is lower than the bottom wall of a magnetic bead coating section, capillary action is needed to suck up the sample in the recess. Moreover, due to the presence of the cut-off groove and the barrier portion, the sample can only enter the magnetic bead coating section from a flow guiding portion, is fully mixed and reacted with a magnetic bead-conjugated ligand, washed with a washing fluid in a washing area, and subjected to luminescence detection in a detection area.

DESCRIPTION OF THE EMBODIMENTS

Figure 1:
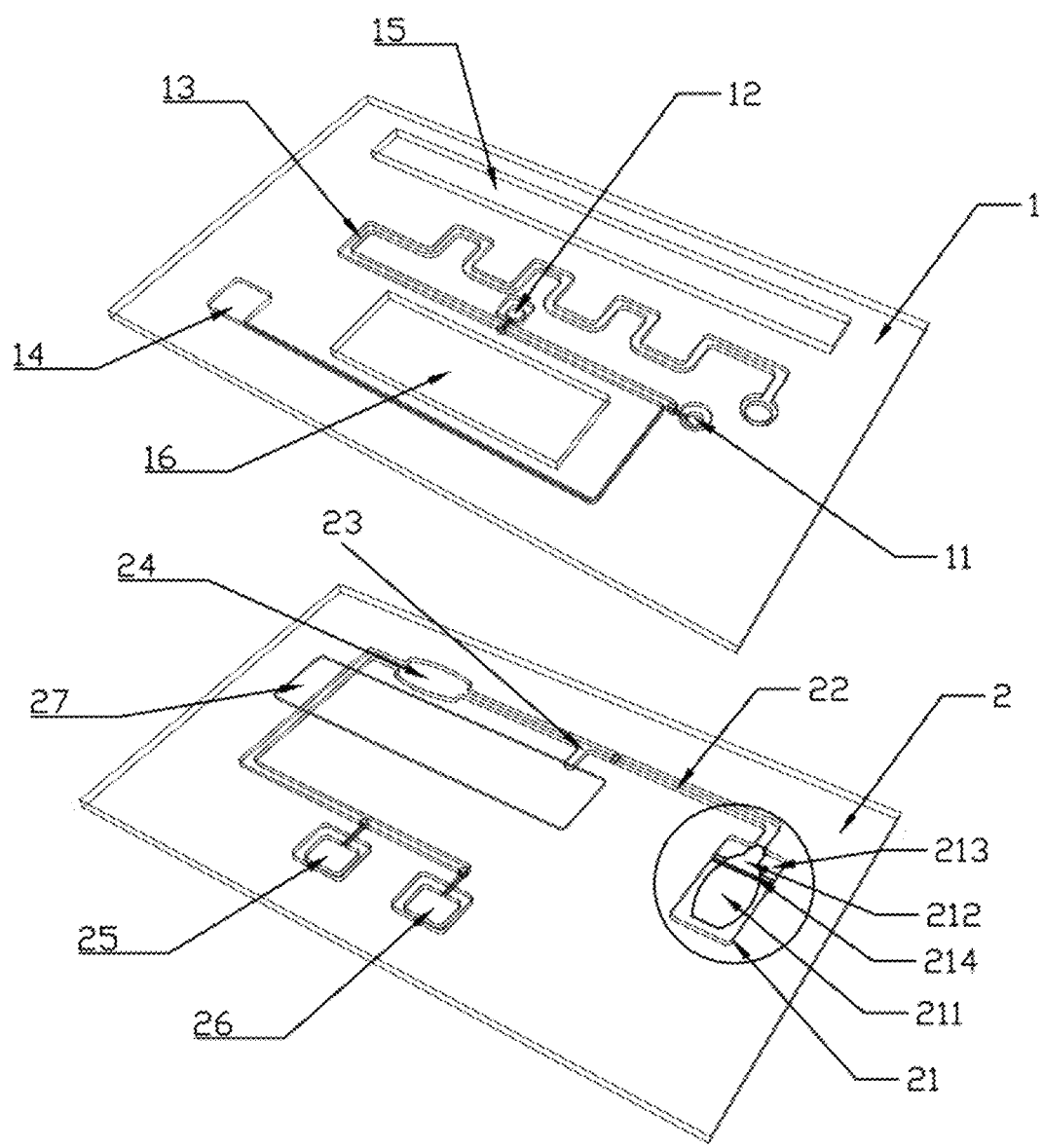
FIG. 1 is a schematic exploded view showing a two-layer microfluidic chip with magnetic bead luminescence provided in an embodiment of the present invention.

To make the objects, technical solutions, and advantages of the present invention clearer, the present invention is described in further detail with reference to accompanying drawings and examples. It should be understood that the specific examples described herein are merely provided for illustrating, instead of limiting the present invention.

In the present invention, a two-layer microfluidic chip with magnetic bead luminescence and a detection system are designed. A sample enters the chip from a sample addition section 11, is mixed with a conjugated ligand in a sample mixing area 13, and then enters a recess 211 in a flow guiding area 21. Because the recess 211 is lower than the bottom wall 221 of a magnetic bead coating section 22, capillary action is needed to suck up the sample in the recess 211. The sample enters the magnetic bead coating section 22 from a flow guiding portion 212, is fully mixed and reacted with a magnetic bead-conjugated ligand, washed with a washing fluid in a washing area 23, and subjected to luminescence detection in a detection area 24.

Embodiment 1

Figure 2:
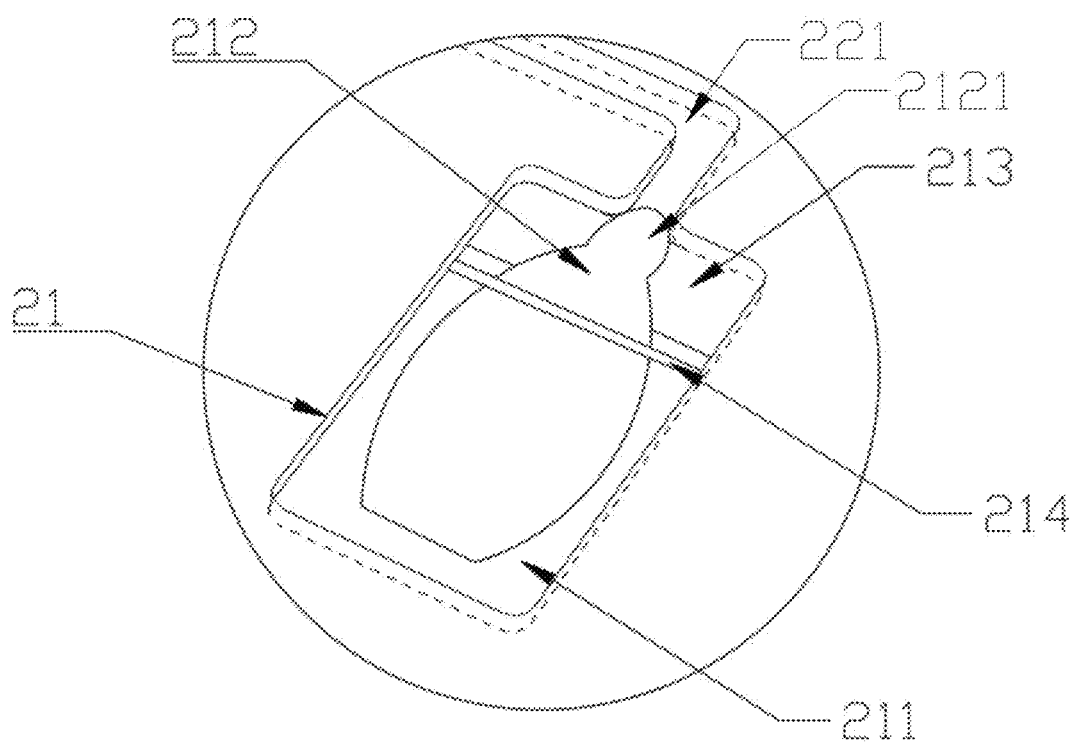
FIG. 2 is a partially enlarged view of FIG. 1.
Figure 2A:
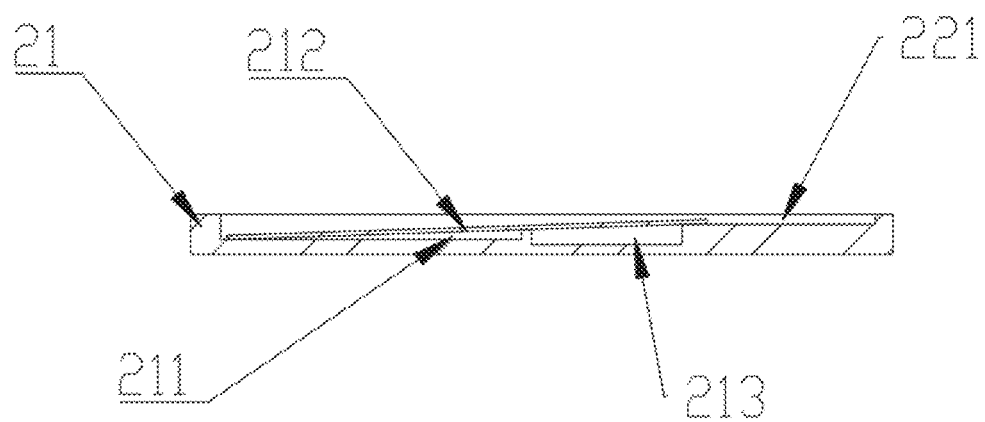
FIG. 2A is a cross sectional view of FIG. 1 showing the positional relationship between a recess in the flow guiding area and a bottom wall of magnetic bead coating section, in which a barrier portion is omitted for clarity.

Referring to FIGS. 1 and 2, Embodiment 1 provides a two-layer microfluidic chip with magnetic bead luminescence, which comprises a top plate 1 and a bottom plate 2 provided on the top plate 1.

The top plate 1 comprises a sample addition section 11, a conjugated ligand storage section 12, and a sample mixing area 13. A conjugated ligand is stored in the conjugated ligand storage section 12, and the sample mixing area 13 is in communication respectively with the sample addition section 11 and the conjugated ligand storage section 12.

The bottom plate 2 comprises a flow guiding area 21 in communication with the sample mixing area 13, a magnetic bead coating section 22 in communication with the flow guiding area 21, a washing area 23 in communication with the magnetic bead coating section 22, a detection area 24 in communication with the washing area 23, and a washing fluid storage section 25 in communication with the washing area 23. The flow guiding area 21 is arranged with a recess 211 that is lower than the bottom wall 221 of the magnetic bead coating section 22 in the height direction, a flow guiding portion 212 fitted to the recess 211 and connecting the magnetic bead coating section 22, a cut-off groove 213 below a front end 2121 of the flow guiding portion 212, and a barrier portion 214 provided on the flow guiding portion 212. The flow guiding portion 212 is optionally a whole blood separation membrane, the barrier portion 214 is optionally plastic paper, the bottom wall of the cut-off groove 213 is also provided with a whole blood separation membrane, and the height of the cut-off groove 213 is lower than the height of the recess 211. A magnetic bead-conjugated ligand solution is stored in the magnetic bead coating section 22, and a washing fluid is stored in the washing fluid storage section 25.

For example, the sample is a whole blood sample. The sample to be tested is transferred to the sample addition section 11. The sample enters the sample mixing area 13 through the sample addition section 11. At this time, the conjugated ligand in the conjugated ligand storage section 12 also enters the sample mixing area 13. The sample is mixed with the conjugated ligand in the sample mixing area 13 and then enters the flow guiding portion 212 in the flow guiding area 21 from the sample mixing area 13. After passing through the flow guiding area 21, the plasma in the sample is separated from the blood cells, the plasma enters the magnetic bead coating section 22 from the flow guiding portion 212, and the blood cells are remained in the flow guiding area 21. Since the recess 211 in the flow guiding area 21 is lower than the bottom wall 221 of magnetic bead coating section 22 and the flow guiding portion 212 is also lower than the bottom wall 221 of the magnetic bead coating section 22 in the height direction, after the sample enters the flow guiding area 21, rather than automatically entering the magnetic bead coating section 22 from the flow guiding portion 212 under the action of gravity, the sample is sucked up from the flow guiding portion 212 by capillary action. In this way, a small volume of sample that can meet the detection requirements can be taken from a large volume of sample to avoid the problem that the large sample volume affects the test results. Moreover, due to the presence of the cut-off groove 213 and the barrier portion 214, when the sample enters the flow guiding area 21, it can only flow over the barrier portion 214; and the sample that does not flow through the flow guiding portion 212 will fall into the cut-off groove 213, whereby the sample can only flow to the capillary channel of the magnetic bead coating section 22 from the flow guiding portion 212. In this way, the flow-through area of the sample flowing into the magnetic bead coating section 22 is confined, to avoid flowing out of the flow guiding portion 212 to cause the test sample to flow to the capillary channel of the magnetic bead coating section 22 from other regions, so that the filtering effect is better and the test result is more accurate. It is worth mentioning that if the test sample is whole blood, red blood cells will not spread from the front end 2121 of the flow guiding portion 212 to the capillary channel of the magnetic bead coating section 22, instead the filtered plasma is sucked into the magnetic bead coating section 22 through the capillary action of the capillary channel.

After the sample is guided to reach the corresponding site of the magnetic bead coating section 22, the analyte in the sample reacts with the magnetic bead-conjugated ligand solution, then the magnetic beads in the magnetic bead-conjugated ligand solution are collected by an external magnet, the sample after reaction is fed to the washing area 23, and the magnetic beads are also driven by the external magnet to enter the washing area 23. At this time, the washing fluid in the washing fluid storage section 25 is released, and the washing fluid enters the washing area 23 to wash the magnetic beads in the sample. The sample then enters the detection area 24 from the washing area 23, and the magnetic beads are also driven by the external magnet to enter the detection area 24. In this way, quantitative detection of the analyte in the sample is realized.

The whole blood separation membrane is arranged in the flow guiding area 21 in advance, where the whole blood separation membrane can separate a fluid from the cells by means of physical pores or biological/chemical reagents, to achieve the separation of the plasma from the red blood cells. As such, the plasma flows to the magnetic bead coating section 22, and the red blood cells are retained on the whole blood separation membrane, thereby reducing the interference of red blood cells on the test results. The biological/chemical reagents include a coagulant, which can interconnect red blood cells to form a clot with increased size. The red blood cells with increased size are more likely to be blocked by the network structure of the whole blood separation membrane, thereby effectively reducing the interference of red blood cells on the test results.

Specifically, the washing fluid is previously stored in the washing fluid storage section 25, and used to wash the magnetic beads to remove non-specifically adsorbed analytes, luminescence markers, and other substances that affect the detection results. The washing fluid mainly comprises a buffering agent, a protein and a surfactant, where the buffering agent comprises, without limitation, a borate, a phosphate, Tris-HCl and an acetate, and the pH of the washing fluid ranges from 6.0 to 10.0. The protein includes, but is not limited to, bovine serum albumin, casein and the like. The surfactant includes, but is not limited to, Tween 20, Tween 80, Triton X-100, polyethylene glycol, and polyvinylpyrrolidone. Preferably, in this embodiment, the washing fluid is a Tris-HCl buffer (pH 7.00) comprising bovine serum albumin, Tween 20 and Proclin300.

In this embodiment, the conjugated ligand storage section 12, the magnetic bead coating section 22, and the washing fluid storage section 25 are sealed chambers, and the sealing material used is an elastic material or a high barrier film, specifically glass, plastic, rubber, aluminum foil or high barrier film, where the sealing material may be composed of a single material or a variety of materials in combination. With physical squeezing, the conjugated ligand storage section 12, the magnetic bead coating section 22, and the washing fluid storage section 25 may be partially crushed to release the stored materials.

Embodiment 2

Referring to FIG. 1, on the basis of Embodiment 1, an air pump 14 communicating with the sample addition section 11 is further provided on the top plate 1 in Embodiment 2. The air pump 14 is a balloon built in the top plate 1. By repeatedly pressing or releasing the balloon, the air in the balloon is allowed to repeatedly enter and exit the sample addition section 11 and the sample mixing area 13, thereby driving the liquid in the top plate 1 to flow.

The air pump 14 is used to evacuate or pressurize the air in the sample mixing area 13 to allow the sample and the conjugated ligand to flow to the sample mixing area 13. By repeatedly evacuating or pressurizing the air in the top plate 1, the sample is thoroughly mixed with the conjugated ligand in the sample mixing area 13, and driven to flow from the sample mixing area 13 to the flow guiding area 21 after mixing.

It should be noted that the air pump 14 needs to work in a sealed environment. In order to seal the interior of the chip, after the sample is added via a sample addition port, a lid is closed, to seal the interior of the chip and ensure the driving effect of the air pump 14.

Embodiment 3

Referring to FIG. 1, on the basis of Embodiment 2, the top plate 1 has an elastic member provided at a corresponding position of the air pump 14 and the sample mixing area 13 in Embodiment 3. The elastic member is optionally adhered to one side of the top plate 1 that is adjacent to the bottom plate 2. The elastic member can impart elasticity to the air pump 14 and the sample mixing area 13.

Embodiment 4

Referring to FIG. 1, on the basis of Embodiment 2, a porous elastic member that may be a sponge is provided inside the air pump 14 in Embodiment 4. The air pump 14 is repeatedly pressed, and the press force is removed after the air pump 14 is pressed. The porous elastic member can provide a rebound force to the pump face of the air pump 14, so that the pump face becomes tight. The porous elastic member has a plurality of pores, such that the porous elastic member can reduce the volume inside the air pump 14 and contribute to the further miniaturization of the air pump 14.

Embodiment 5

Referring to FIG. 1, on the basis of Embodiment 1, the sample addition section 11 includes a sample addition port and a lid for opening or closing the sample addition section in Embodiment 5.

When the lid is opened, the sample can be externally added via the sample addition port. After the sample is added, the lid is closed to close the sample addition port.

In particular, the lid is provided with a first clamping piece or a first hole, and a second hole or a second clamping piece is provided at a position adjacent to the sample addition port. The first clamping piece mates with the second hole, or the first hole mates with the second clamping piece, to close the sample addition port by the lid. In addition, the lid is provided with a sealing member adaptable to the sample addition port. When the lid is closed, the sealing member is simultaneously inserted into the sample addition port to prevent the sample from leaking out of the sample addition port.

Moreover, the sample addition section 11 also includes a rubber ring provided on the sample addition port. Since the sample is often added externally through a pipette tip, the rubber ring is elastic, which contributes to sealing with the pipette tip, so that the sample can be added from the sample addition port smoothly.

Embodiment 6

On the basis of Embodiment 1, both the top plate 1 and the bottom plate 2 are provided with a limiting notch at a position corresponding to each other in Embodiment 6. The limiting notch is a notch arranged at one end of top plate 1 and the bottom plate 2, which is not shown in the figure. During detection with the two-layer microfluidic chip with magnetic bead luminescence, in order to prevent the two-layer microfluidic chip with magnetic bead luminescence from deflection, it is necessary to limit the two-layer microfluidic chip with magnetic bead luminescence. The limiting notch mates with an external limiting structure, to fix the chip firmly during the detection process to prevent it from deflection, thereby ensuring the smooth progress of the detection.

Embodiment 7

Referring to FIG. 1, on the basis of Embodiment 1, the top plate 1 is provided with a first buckle or a first slot, and the bottom plate 2 is provided with a second slot or a second buckle in Embodiment 7. The first buckle mates with the second slot, or the first slot mates with the second buckle, so that the top plate 1 and the bottom plate 2 are fastened. Through the above-mentioned fastening method, the top plate 1 and the bottom plate 2 are detachably assembled, which is beneficial to the inspection or replacement by an operator. After being fastened, the top plate 1 and the bottom plate 2 can be firmly fixed to each other.

Of course, the top plate 1 and the bottom plate 2 can also be attached to each other in other ways, which are not elaborated here.

Embodiment 8

Figure 3:
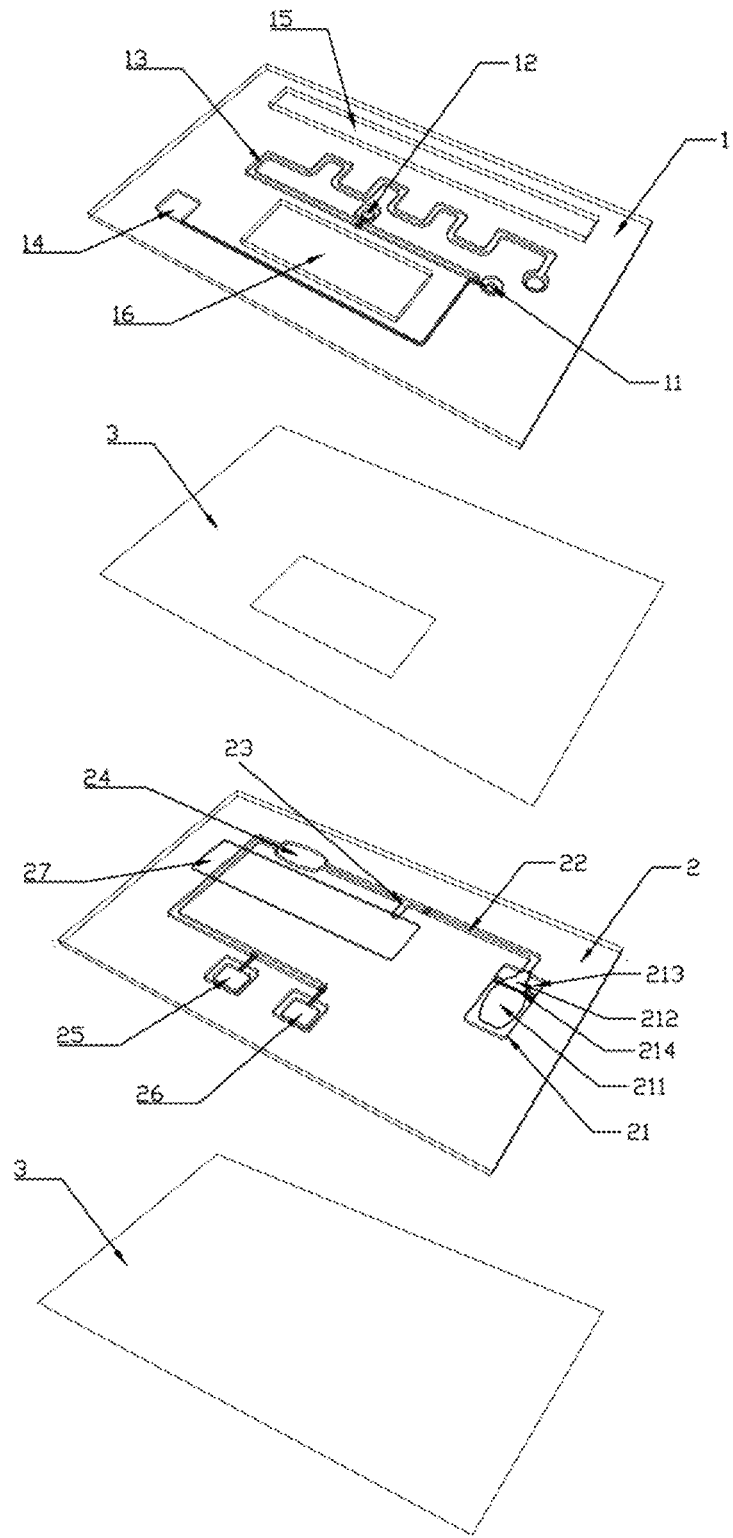
FIG. 3 is another schematic exploded view showing a two-layer microfluidic chip with magnetic bead luminescence provided in an embodiment of the present invention.

Referring to FIG. 3, on the basis of Embodiment 1, a part of or the entire surface at at least one side of the bottom plate 2 is provided with a single-sided adhesive material 3, and the single-sided adhesive material 3 may be a single-sided adhesive tape. Preferably, the single-sided adhesive material 3 is provided on both sides of the bottom plate 2, and the single-sided adhesive material 3 serves to seal the bottom plate 2. In this embodiment, the single-sided adhesive material 3 is provided with a clearance region at a position corresponding to the washing fluid storage section.

Embodiment 9

Referring to FIG. 1, on the basis of Embodiment 1, a product label is provided on the surface of the top plate 1 in Embodiment 9, and related description of the chip is provided on the product label, such as the chip name, the target to be detected by the chip, and the like.

Moreover, a two-dimensional code label is provided on the surface of the top plate 1 or the bottom plate 2, and a camera on an external detection device can scan the two-dimensional code label, to read relevant data, such as the chip name, the target to be detected by the chip, and the calibration information of the product. It should be noted that the position of the two-dimensional code label depends on the position of orientation of the camera on the external detection device.

Embodiment 10

Referring to FIG. 1, on the basis of Embodiment 1, the top plate 1 is provided with a magnetic attraction clearance hole 15 on a corresponding track in communication with the magnetic bead coating section 22, the washing area 23 and the detection area 24 in Embodiment 10. An external magnet moves along a set direction of the magnetic attraction clearance hole 15 to drive the magnetic beads to move sequentially along the magnetic bead coating section 22, the washing area 23 and the detection area 24. Furthermore, the arrangement of the magnetic attraction clearance hole 15 allows the magnet to be closer to the bottom plate 2 to avoid the intervention of the top plate 1 between the bottom plate 2 and the magnet, which greatly improves the reliability of the magnetic attraction.

Embodiment 11

Referring to FIG. 1, on the basis of Embodiment 1, the bottom plate 2 is provided with a waste container 27 communicating with the washing area 23 in Embodiment 11. The waste container 27 can collect the waste liquid after washing and reaction, thereby reducing the interference of waste liquid on the final detection and effectively improving the detection accuracy. A plurality of waste container 27 may be provided.

Embodiment 12

Referring to FIG. 1, on the basis of Embodiments 1 to 11, the bottom plate 2 further includes a luminescence liquid storage section 26 in communication with the detection area 24 in Embodiment 12, where a luminescence liquid is stored in the luminescence liquid storage section 26.

The sample enters the detection area 24 after being washed in the washing area 23. At this time, the luminescence liquid in the luminescence liquid storage section 26 is released, and the luminescence liquid reacts with the sample to emit a light signal, and an external detection device detects the intensity of the light signal.

The luminescence liquid is previously stored in the luminescence liquid storage section 26 and used to further wash the magnetic beads or enhance the luminescence signal. The luminescence liquid comprises a substrate solution and a luminescence enhancing solution. The substrate solution may be an acidic solution containing luminol or an acidic solution containing adamantane. The luminescence enhancing solution may be an alkaline solution containing a benzene derivative.

Notably, considering that the substrate solution and the luminescence enhancing solution are conveniently not stored in mixture for a long time, the luminescence liquid storage section 26 is arranged to have a first luminescence liquid storage section and a second luminescence liquid storage section. The substrate solution is stored in the first luminescence liquid storage section, and the luminescence enhancing solution is stored in the second luminescence liquid storage section. Further, a luminescence liquid mixing area is provided on the bottom plate 2, and the luminescence liquid mixing area is in communication respectively with the detection area 24, the first luminescence liquid storage section, and the second luminescence liquid storage section. When released from the first luminescence liquid storage section and the second luminescence liquid storage section, the substrate solution and the luminescence enhancing solution enter the luminescence liquid mixing area, are mixed with each other, and then enter the detection area 24 after being mixed uniformly.

The luminescence liquid storage section 26 is a sealed chamber, and the sealing material used is an elastic material or a high barrier film, specifically glass, plastic, rubber, aluminum foil or high barrier film, where the sealing material may be composed of a single material or a variety of materials in combination. With physical squeezing, the luminescence liquid storage section 26 may be partially crushed to release the stored luminescence liquid.

The conjugated ligand is previously stored in the conjugated ligand storage section 12. When the conjugated ligand is an enzyme-conjugated ligand, the enzyme includes one or more of horseradish peroxidase and alkaline phosphatase; and the ligand includes one or more of an antigen, an antibody, a hapten, and a nucleic acid. The magnetic bead-conjugated ligand solution is previously stored in the magnetic bead coating section 22, and the magnetic bead-conjugated ligand solution comprises magnetic beads, a carbohydrate, a buffering agent, a protein, a surfactant and a preservative, where the magnetic beads include, but are not limited to, ferric oxide and ferroferric oxide.

When the conjugated ligand is an enzyme-conjugated ligand, the enzyme binds to or competes the analyte in the sample to form an enzyme-conjugated ligand. The magnetic beads bind to or compete the analyte in the sample to form a magnetic bead-conjugated ligand. The two ligands may be the same or different. The ligand used in the magnetic bead-conjugated ligand solution and the enzyme-conjugated ligand comprises a nucleic acid, an antigen, a monoclonal antibody, a polyclonal antibody and a hormone receptor. The analyte in the sample comprises DNA, small molecules (drugs or narcotics), antigens, antibodies, hormones, antibiotics, bacteria or viruses and other biochemical markers.

In this embodiment, the conjugated ligand may bind to (e.g. double antibody sandwich method) or compete with (e.g., competition method) the magnetic bead-conjugated ligand solution. The ligand in the enzyme-conjugated ligand may be the same or different from that in the magnetic bead-conjugated ligand solution. Preferably, in one embodiment of the present invention, two different antibodies are used as the ligand in the conjugated ligand and the ligand in the magnetic bead-conjugated ligand solution to detect the analyte by a dual antibody sandwich method. In another embodiment of the present invention, an antigen and an antibody are respectively used as the ligand in the conjugated ligand and the ligand in the magnetic bead-conjugated ligand solution to detect the analyte by a competition method.

Embodiment 13

Referring to FIG. 1, on the basis of Embodiment 12, the top plate 1 is provided with a washing fluid clearance hole and a luminescence liquid clearance hole at positions corresponding to the washing fluid storage section 25 and the luminescence liquid storage section 26 on the bottom plate 2 in Embodiment 13.

Because the washing fluid storage section 25 and the luminescence liquid storage section 26 are often arranged to have a certain shape, such as a cylindrical shape, in order to adapt to the shapes of washing fluid storage section 25 and the luminescence liquid storage section 26 and avoid local protrusion of the chip, a washing fluid clearance hole and a luminescence liquid clearance hole are set on top plate 1.

In this embodiment, the washing fluid clearance hole and the luminescence liquid clearance hole form the clearance hole 16.

Embodiment 14

Referring to FIG. 1, on the basis of Embodiments 1 to 11, a luminescence agent is stored in the conjugated ligand storage section 12 in Embodiment 14. That is to say, the conjugated ligand is a fluorescence agent-conjugated ligand. The fluorescence agent can be one or more of acridinium ester, ABEI, a fluorescent dye, a fluorescent protein, and fluorescent microspheres. The ligand can be one or more of an antigen, an antibody, a hapten and a nucleic acid. Acridinium ester, and ABEI can directly emit light after reaction with the luminescence liquid; and the fluorescent dye, fluorescent protein and fluorescent microspheres need an excitation light source, but not luminescence liquid.

When the conjugated ligand is a fluorescence agent-conjugated ligand, the fluorescence agent binds to or competes the analyte in the sample to form a luminescence agent-conjugated ligand. The magnetic beads bind to or compete the analyte in the sample to form a magnetic bead-conjugated ligand. The two ligands may be the same or different. The ligand used in the magnetic bead-conjugated ligand solution and the fluorescence agent-conjugated ligand comprises a nucleic acid, an antigen, a monoclonal antibody, a polyclonal antibody and a hormone receptor. The analyte in the sample comprises DNA, small molecules (drugs or narcotics), antigens, antibodies, hormones, antibiotics, bacteria or viruses and other biochemical markers.

In this embodiment, the conjugated ligand may bind to (e.g. double antibody sandwich method) or compete with (e.g., competition method) the magnetic bead-conjugated ligand solution. The ligand in the fluorescence agent-conjugated ligand may be the same or different from that in the magnetic bead-conjugated ligand solution. Preferably, in one embodiment of the present invention, two different antibodies are used as the ligand in the conjugated ligand and the ligand in the magnetic bead-conjugated ligand solution to detect the analyte by a dual antibody sandwich method.

Embodiment 15

Embodiment 15 provides a two-layer microfluidic detection system with magnetic bead luminescence. The detection system comprises a two-layer microfluidic chip with magnetic bead luminescence as described in Embodiments 1-14; a magnet unit for driving the magnetic beads in the magnetic bead-conjugated ligand solution to move; a squeezing unit for crushing the conjugated ligand storage section 12 and the washing fluid storage section 25 so that the conjugated ligand and the washing fluid flow out; and a detection unit for detecting the sample in the detection area 24.

The magnet unit includes a magnet and a drive element for driving the movement of the magnet. The drive element may be a linear motor. An output shaft of the linear motor is fixedly connected to the magnet. After the linear motor is activated, the output shaft of the linear motor extends to drive the magnet to move. The magnet attracts the magnetic beads and drives the magnetic beads to move.

The squeezing unit can be a linear motor. After the linear motor is activated, the output shaft extends to squeeze the conjugated ligand storage section 12 and washing fluid storage section 25, so that the conjugated ligand and the washing fluid flow out. Of course, a squeeze part can also be fixed on the output shaft of the linear motor, and the squeeze part matches each of the storage sections in size and shape. One or more linear motor may be present. The squeeze part is driven by the output shaft of the linear motor, and then the squeeze part squeezes the conjugated ligand storage section 12 and the washing fluid storage section 25 to allow the conjugated ligand and the washing fluid to flow out, respectively.

The detection unit can be a photodiode, a photomultiplier tube or an avalanche photodiode. After mixing and reaction as described above, the sample enters the detection area, and the mixed sample will emit a light signal. The detection unit collects the light signal emitted, and obtains the detection result for the sample according to the intensity of the light signal emitted.

When the two-layer microfluidic chip with magnetic bead luminescence is provided with the air pump 14, the squeezing unit can also be used to press the air pump 14, so as to drive the liquid on the top plate 1 to flow.

When the two-layer microfluidic chip with magnetic bead luminescence is provided with the luminescence liquid storage section 26, the squeezing unit can also be used to squeeze the luminescence liquid storage section 26, to allow the luminescence liquid to flow out.

The present invention has been described in detail with reference to preferred embodiments, which however are not intended to limit the present invention. Any modifications, equivalent improvements and substitutions can be made without departing from the spirit and principle of the present invention, which are all fall within the protection scope of the present invention.

What is claimed is:

1. A two-layer microfluidic chip with magnetic bead luminescence, comprising:
   a top plate, comprising a sample addition section, a conjugated ligand storage section, and a sample mixing area, wherein a conjugated ligand is stored in the conjugated ligand storage section, and the sample mixing area is in communication respectively with the sample addition section and the conjugated ligand storage section; and
   a bottom plate provided on the top plate, comprising a flow guiding area in communication with the sample mixing area, a magnetic bead coating section in communication with the flow guiding area, a washing area in communication with the magnetic bead coating section, a detection area in communication with the washing area, and a washing fluid storage section in communication with the washing area, wherein the flow guiding area is arranged with a recess that is lower than a bottom wall of the magnetic bead coating section in the height direction, a flow guiding portion fitted to the recess and connecting the magnetic bead coating section, a cut-off groove below a front end of the flow guiding portion, and a barrier portion provided on the flow guiding portion; and a magnetic bead-conjugated ligand is stored in the magnetic bead coating section, and a washing fluid is stored in the washing fluid storage section.

2. The two-layer microfluidic chip with magnetic bead luminescence according to claim 1, wherein the top plate further comprises an air pump communicating with the sample addition section.

3. The two-layer microfluidic chip with magnetic bead luminescence according to claim 2, wherein the top plate has an elastic member provided at a corresponding position of the air pump and the sample mixing area.

4. The two-layer microfluidic chip with magnetic bead luminescence according to claim 2, wherein a porous elastic member is provided inside the air pump.

5. The two-layer microfluidic chip with magnetic bead luminescence according to claim 1, wherein the sample addition section comprises a sample addition port and a lid for opening or closing the sample addition port, and the sample addition section further includes a rubber ring provided on the sample addition port.

6. The two-layer microfluidic chip with magnetic bead luminescence according to claim 1, wherein both the top plate and the bottom plate are provided with a limiting notch at a position corresponding to each other.

7. The two-layer microfluidic chip with magnetic bead luminescence according to claim 1, wherein the top plate is provided with a first buckle or a first slot, and the bottom plate is provided with a second slot or a second buckle; and the first buckle mates with the second slot, or the first slot mates with the second buckle, so that the top plate and the bottom plate are fastened.

8. The two-layer microfluidic chip with magnetic bead luminescence according to claim 1, wherein a single-sided adhesive material is provided on a part of or the entire surface at at least one side of the bottom plate.

9. The two-layer microfluidic chip with magnetic bead luminescence according to claim 1, wherein a product label is provided on the surface of the top plate or the bottom plate, and a two-dimensional code label is provided on the surface of the top plate or the bottom plate.

10. The two-layer microfluidic chip with magnetic bead luminescence according to claim 1, wherein the top plate is provided with a magnetic attraction clearance hole on a corresponding track in communication with the magnetic bead coating section, the washing area and the detection area.

11. The two-layer microfluidic chip with magnetic bead luminescence according to claim 1, wherein the bottom plate further comprises a waste container communicating with the washing area.

12. The two-layer microfluidic chip with magnetic bead luminescence according to claim 1, wherein the bottom plate also comprises a luminescence liquid storage section communicating with the detection area, and a luminescence liquid is stored in the luminescence liquid storage section.

13. The two-layer microfluidic chip with magnetic bead luminescence according to claim 12, wherein the top plate is provided with a washing fluid clearance hole and a luminescence liquid clearance hole at a position corresponding to the washing fluid storage section and the luminescence liquid storage section.

14. The two-layer microfluidic chip with magnetic bead luminescence according to claim 1, wherein a fluorescence liquid is stored in the conjugated ligand storage section.

15. A two-layer microfluidic detection system with magnetic bead luminescence, comprising:
   a two-layer microfluidic chip with magnetic bead luminescence according to claim 1;
   a magnet unit for driving the magnetic beads in the magnetic bead-conjugated ligand solution to move;
   a squeezing unit for crushing the conjugated ligand storage section and the washing fluid storage section so that the conjugated ligand and the washing fluid flow out; and
   a detection unit for detecting a light signal emitted from the detection area.

* * * * *